(12) United States Patent
Catani et al.

(10) Patent No.: US 11,306,114 B2
(45) Date of Patent: Apr. 19, 2022

(54) PROCESS FOR SEPARATION, ISOLATION AND CHARACTERIZATION OF STEVIOL GLYCOSIDES

(71) Applicant: Heartland Consumer Products, LLC, Carmel, IN (US)

(72) Inventors: Steven J. Catani, Athens, GA (US); Juan Navia, Doylestown, PA (US)

(73) Assignee: Heartland Consumer Products LLC, Carmel, IN (US)

( * ) Notice: Subject to any disclaimer, the term of this patent is extended or adjusted under 35 U.S.C. 154(b) by 0 days.

(21) Appl. No.: 14/624,758

(22) Filed: Feb. 18, 2015

(65) Prior Publication Data

US 2015/0257424 A1    Sep. 17, 2015

Related U.S. Application Data

(60) Provisional application No. 61/941,018, filed on Feb. 18, 2014.

(51) Int. Cl.
| | | |
|---|---|---|
| C07H 1/08 | (2006.01) | |
| C07H 15/24 | (2006.01) | |
| A23L 27/30 | (2016.01) | |

(52) U.S. Cl.
CPC ............... *C07H 1/08* (2013.01); *A23L 27/33* (2016.08); *C07H 15/24* (2013.01); *A23V 2002/00* (2013.01)

(58) Field of Classification Search
CPC ........... C07H 1/08; C07H 15/24; A23L 27/33; A23V 2002/00
USPC ........................................ 426/548, 650, 478
See application file for complete search history.

(56) References Cited

U.S. PATENT DOCUMENTS

| | | |
|---|---|---|
| 4,082,858 A | 4/1978 | Morita et al. |
| 4,219,571 A | 8/1980 | Miyake |
| 4,361,697 A | 11/1982 | Dobberstein et al. |
| 4,612,942 A | 9/1986 | Dobberstein et al. |
| 4,892,938 A | 1/1990 | Giovanetto |
| 5,962,678 A | 10/1999 | Payzant et al. |
| 5,972,120 A | 10/1999 | Kutowy et al. |
| 7,807,206 B2 | 10/2010 | Magomet et al. |
| 7,838,044 B2 | 11/2010 | Abelyan et al. |
| 7,862,845 B2 | 1/2011 | Magomet et al. |
| 7,927,851 B2 | 4/2011 | Brandie et al. |
| 7,964,232 B2 | 6/2011 | Lee |
| 8,257,948 B1 | 9/2012 | Markosyan |
| 8,277,862 B2 | 10/2012 | Lee et al. |
| 8,299,224 B2 | 10/2012 | Abelyan et al. |
| PP23,164 P3 | 11/2012 | Ramon Alvarez Britos |
| 8,318,459 B2 | 11/2012 | Markosyan |
| 8,337,928 B2 | 12/2012 | May et al. |
| PP23,728 P3 | 7/2013 | Ramon Alvarez Britos |
| 8,520,527 B2 | 8/2013 | Belmont et al. |
| 2006/0142555 A1 | 6/2006 | Jonnala |
| 2009/0004355 A1 | 1/2009 | Catani |
| 2009/0017185 A1 | 1/2009 | Catani |
| 2010/0285201 A1 | 11/2010 | Catani et al. |
| 2011/0183056 A1 | 7/2011 | Morita et al. |
| 2011/0256588 A1 | 10/2011 | Lee et al. |
| 2012/0058247 A1* | 3/2012 | Shi ............................ A23L 2/60 426/658 |
| 2012/0201940 A1 | 8/2012 | Catani et al. |
| 2012/0201952 A1 | 8/2012 | Catani et al. |
| 2012/0269954 A1 | 10/2012 | Bridges et al. |
| 2013/0071339 A1 | 3/2013 | Markosyan |
| 2013/0071537 A1 | 3/2013 | Shi et al. |
| 2013/0309389 A1 | 11/2013 | Carlson et al. |
| 2013/0347140 A1 | 12/2013 | Wang |
| 2014/0004248 A1 | 1/2014 | Zhang et al. |
| 2014/0243514 A1 | 8/2014 | Brower, III et al. |
| 2014/0335253 A1 | 11/2014 | Shi et al. |
| 2014/0335254 A1 | 11/2014 | Shi et al. |
| 2014/0335264 A1 | 11/2014 | Shi et al. |
| 2014/0335265 A1 | 11/2014 | Shi et al. |
| 2015/0017284 A1 | 1/2015 | Prakash et al. |

FOREIGN PATENT DOCUMENTS

| | | |
|---|---|---|
| CN | 101366496 A | 2/2009 |
| CN | 102127129 A | 7/2011 |
| CN | 102406113 A | 4/2012 |
| CN | 103012516 A | 4/2013 |
| GB | 1543167 | 3/1979 |
| JP | 1989131191 A | 5/1989 |
| JP | 2000201700 A | 7/2000 |

(Continued)

OTHER PUBLICATIONS

Bart and co-authors (Continuous chromatographic separation of fructose, mannitol and sorbitol. Chemical Engineering and Processing 35 (1996) 459-471).
Brandie et al. (2002) Plant Molecular Biology 50: 613-622.
Bubnik and co-authors in "Application of continuous chromatographic separation in sugar processing", Journal of Food Engineering 61 (2004) 509-513.
Chang S. S. et al. (1983) Stability studies of Stevioside and Rebaudioside A in carbonated beverages. J. Agric. Food Chem. 31: 409-412.
Eom et al. (J. Chromatogr. A 1217 (2010) 4347-4354).
David J. Midmore and Andrew H. Rank A new rural industry—Stevia—to replace imported chemical sweeteners. A report for the Rural Industries Research and Development Corporation, Aug. 2002; RIRDC Web Publication No. W02/022, RIRDC Project No. UCQ-16A.
Grant E. DuBois and Indra Prakash in Annu. Rev. Food Sci. Technol. (2012), 3:353-380 (Non-Caloric Sweeteners, Sweetness Modulators, and Sweetener Enhancers).

(Continued)

*Primary Examiner* — Leslie A Wong
(74) *Attorney, Agent, or Firm* — Taft Stettinius & Hollister LLP; Joseph M. Bennett-Paris

(57) ABSTRACT

A comprehensive process for the separation, isolation and characterization of a combination of two or more steviol glycosides from extract of *Stevia rebaudiana* plants and their use in sweetening compositions are disclosed. Combinations of two or more steviol glycosides from *Stevia rebaudiana* are characterized. The combinations of two or more steviol glycosides can be used as sweetness enhancers, flavor enhancers and sweeteners in foods, beverages, cosmetics and pharmaceuticals. A method for isolating combinations of two or more steviol glycosides is also disclosed.

5 Claims, 7 Drawing Sheets

(56) References Cited

FOREIGN PATENT DOCUMENTS

| | | | |
|---|---|---|---|
| JP | 2003061700 A | 3/2003 | |
| JP | 2008208284 A | 9/2008 | |
| JP | 2011051909 A | 3/2011 | |
| JP | 2011105757 A | 6/2011 | |
| JP | 2013165690 A | 8/2013 | |
| WO | 2009140394 A1 | 11/2009 | |

OTHER PUBLICATIONS

Hilbrig et al. ("Continuous annular chromatography", Journal of Chromatography B, 790 (2003) 1-15).

Kitahata S. et al. (1989) Production of rubusoside derivatives by transglycosylation of various β-galactosidase. Agric. Biol. Chem. 53: 2923-2928.

Kovylyaeva G.I. et al. "Glycosides from Stevia rebaundiana", Chemistry of Natural Compounds, Kluwer Academic Publishers—Consultants Bureau, vol. 43, No. 1, Jan. 1, 2007, pp. 81-85, XP019499675, ISSN: 1573-833, DOI: 10.1007/S10600-007-0037-X. p. 83-84, table 1.

Lobov S. V. et al. (1991) Enzymatic production of sweet stevioside derivatives: transglycosylation by glucosidases. Agric. Biol. Chem. 55: 2959-2965.

Ohta et al., Characterization of novel steviol glycosides from leaves of Stevia rebaudiana morita, J. Appl. Glycosci., 57, 199-209 (2010).

Phillips K. C. (1989) Stevia: steps in developing a new sweetener. In: Grenby T. H. ed. Developments in sweeteners, vol. 3. Elsevier Applied Science, London. 1-43.

Prakash et al. (2008) Development of Rebiana®, a natural, non-caloric sweetener. Food Chem. Toxicol., 46, S75-S82.

Richman et al., (2005) The Plant Journal 41, 55-67.

Richman et al. (1999) The Plant Journal 19(4), 411-421.

Tanaka O. (1987) Improvement of taste of natural sweeteners. Pure Appl. Chem. 69:675-683.

Wölwer-Rieck U. The Leaves of Stevia rebaudiana (Bertoni), Their Constituents and the Analysis Thereof: A Review. J. Agric. Chem. 2012, 60,886-895).

Yamamoto K. et al. (1994) Effective production of glucosyl-stevioside by α-1,6-transglucosylation of dextran dextranase. Biosci. Biotech. Biochem. 58: 1657-1661.

Zimmerman, Tandem mass spectrometric fragmentation patterns of known and new steviol glycosides with structure proposals, Rapid Commun. Mass. Spectrom. 2011 ,25, 1575-1582.

Rajendran and co-authors, "Simulated Moving Bed Chromatography for the Separation of Enantiomers", Journal of Chromatography A, 1216 (2009), 709-738.

* cited by examiner

Steviol glycoside aglycone structure with indicated location of glycosylation (R1 and R2)

PROCESS FOR SEPARATION, ISOLATION AND CHARACTERIZATION OF STEVIOL GLYCOSIDES

CROSS REFERENCE TO RELATED APPLICATIONS

This application claims priority from U.S. Provisional Application Ser. No. 61/941,018, filed Feb. 18, 2014, the contents of which are hereby incorporated by reference in their entirety.

FIELD OF THE INVENTION

The invention relates to a comprehensive process for the separation, isolation and characterization of steviol glycosides from the extract of the *Stevia rebaudiana* plants and their use in sweetening compositions.

BACKGROUND OF THE INVENTION

Nowadays, sugar alternatives are receiving increasing attention due to awareness of many diseases in conjunction with consumption of high-sugar foods and beverages. However, many artificial sweeteners such as dulcin, sodium cyclamate and saccharin were banned or restricted in some countries due to concerns on their safety. Therefore, non-caloric sweeteners of natural origin are becoming increasingly popular.

*Stevia rebaudiana* Bertoni is a perennial shrub of the Asteraceae (Compositae) family native to certain regions of South America. The leaves of the plant contain from 10 to 20% of diterpene glycosides, which are around 150 to 450 times sweeter than sugar. The leaves have been traditionally used for hundreds of years in Paraguay and Brazil to sweeten local teas and medicines.

Typical practice is to grow plants during the warm part of the year, then harvest before the plants flower. David J. Midmore and Andrew H. Rank ("A new rural industry—*Stevia*—to replace imported chemical sweeteners. A report for the Rural Industries Research and Development Corporation, August 2002; RIRDC Web Publication No. W02/022, RIRDC Project No UCQ-16A) report multiple crops per year are possible in warmer climates such as Brazil, Paraguay, India or Indonesia. "Commercial yield figures are not reported other than in general terms, e.g. 1,600-2,000 kg dried leaves/ha/year. Experimental yields suggest that systems with multiple harvests a year will give higher yields." This yield refers to mass of dried plant, not to optimization of steviol glycoside per hectare per harvest. By leveraging improved analytical methods, and good agronomic development of plants selected for improved steviol glycoside yield per hectare, and by coordinating plant maturation within a given geographic region with staggered harvesting, improvements in the post-harvest steviol glycoside yield per harvest season can be accomplished.

Midmore and Rank go on to report "The usual procedure is to harvest the whole crop green and transport it to drying facilities: sun drying or (artificial) drying kilns. With low humidity, sun drying of a thin layer of cut plants can be quite rapid (9-10 hours) to reduce plant moisture from approximately 80% to 10% [116]. Kiln drying can take two days [37]. Fast drying is likely to give 'better quality' dried leaves. If cut plant material is not dried quickly leaf quality can deteriorate by oxidation, losing up to one third of stevioside content after three days [116]. High temperature during artificial drying can also lead to loss of content. A green dried leaf colour is desirable and represents good quality". We have enabled improvement in this practice by staggering harvest and timing it to extractive processing of wet (i.e., fresh, undried) leaves that are not subjected to any drying process. This improvement confers the dual benefits of reducing glycoside loss during drying and the savings in processing costs by obviating the need for a drier.

Dried *Stevia* leaves are reported to contain approximately 5% to 9% moisture, 10% to 20% protein, 35% to 62% carbohydrates, 3% to 5% fats (principally palmitic, linolenic and linoleic acids), 7% to 13% ash and several volatile components including spathulenol, beta-pinene, beta-caryophyllene, and caryophyllene oxide. *Stevia* is also a rich source of oxalic acid (see Wölwer-Rieck U. The Leaves of *Stevia rebaudiana* (Bertoni), Their Constituents and the Analysis Thereof: A Review. J. Agric. Chem. 2012, 60, 886-895). These components can affect the flavor aroma of the sweetener if not removed or reduced to a substantially low level. As a result, the isolation of individual high-purity *Stevia* sweeteners has entailed extensive processing including treatment with various resins, separation using organic solvents, and crystallization to render a product of suitable taste and quality.

At present there are more than 230 *Stevia* species with significant sweetening properties. The plant has been successfully grown under a wide range of conditions from its native subtropics to the cold northern latitudes. The composition of steviol glycosides can be modified by directed plant breeding. Whereas native plant species had stevioside as a predominant steviol glycosides modern cultivars have been selected for increased Rebaudioside A content, which is considered a better quality sweetener than stevioside. *Stevia rebaudiana* produces a number of other steviol glycosides that also feature high intensity sweetness and sensory properties, in some cases superior to those of many other naturally occurring high potency sweeteners. Steviol glycosides are not metabolized for energy in the human digestive system, and can be used for sweetening foods without adding calories wherever sugar is used. They are suitable for diabetic and low calorie diets.

The above-mentioned glycosides have a common aglycone, steviol, and differ by the number and type of carbohydrate residues at the $C_{13}$ and $C_{19}$ positions (R2 and R1 respectively in FIG. 1). The leaves of *Stevia* are able to accumulate up to 10-20% (on dry weight basis) steviol glycosides. The major glycosides found in native *Stevia* leaves are Rebaudioside A (2-10%), Stevioside (2-10%), and Rebaudioside C (1-2%). Other glycosides, such as Rebaudioside B, D, E, and F, Steviolbioside and Rubusoside, are also found at lower levels (less than 1%). Still other glycosides have been recently reported by Ohta, et al. in J. Appl. Glycosci. (2010) 57:199-209.

Two major glycosides—Stevioside and Rebaudioside A, were extensively studied and characterized in terms of their suitability as commercial high intensity sweeteners. For example, stability studies in carbonated beverages confirmed their heat and pH stability. Chang S. S. et al. (1983) Stability studies of Stevioside and Rebaudioside A in carbonated beverages. J. Agric. Food Chem. 31: 409-412. Even in a highly purified state, these steviol glycosides still possess undesirable taste attributes such as bitterness, sweet aftertaste, licorice flavor, etc. One of the main obstacles for the successful commercialization of *Stevia* sweeteners are these undesirable taste attributes. It was shown that these flavor notes become more prominent as the concentration of steviol glycoside increases (Prakash et al. (2008) Development of Rebiana®, a natural, non-caloric sweetener. Food Chem. Toxicol., 46, S75-S82).

Rebaudioside A has shown the least astringent, the least bitter, and the least persistent aftertaste thus possessing favorable sensory attributes as compared to known steviol glycosides (Tanaka O. (1987) Improvement of taste of natural sweeteners. Pure Appl. Chem. 69:675-683; Phillips K. C. (1989) Stevia: steps in developing a new sweetener. In: Grenby T. H. ed. Developments in sweeteners, vol. 3. Elsevier Applied Science, London. 1-43).

U.S. Published Application No. 2013347140 to Wang discloses a method of breeding Stevia plants having high content of Rebaudioside A.

U.S. Pat. Nos. PP23,164 and PP23,728 disclose cultivars of Stevia named AKH L1 and AKH L4. The cultivars have high rebaudioside A content.

Methods for the extraction and purification of sweet glycosides from the Stevia rebaudiana plant using water or organic solvents are described in, for example, U.S. Pat. Nos. 4,361,697; 4,082,858; 4,892,938; 5,972,120; 5,962,678; 7,838,044 and 7,862,845.

Dobberstein and Ahmed (U.S. Pat. No. 4,361,697) and Morita et al. (U.S. Pat. No. 4,082,858) disclose the silica chromatography of steviol glycosides. Giovenatto (U.S. Pat. No. 4,892,938) employs calcium hydroxide to clarify a crude extract of Stevia sweeteners, followed by filtration or centrifugation. This precipitate is treated with a strongly acidic ion exchange resin and subsequently with a weakly basic ion exchange resin, filtered and dried. Magomet and others (U.S. Pat. No. 7,862,845) also teach the isolation of partially purified steviol glycosides by treatment of a crude extract with calcium salts, filtration of the crude slurry, followed by crystallization of Rebaudioside A from a methanol-water mixture. Abelyan et al. (U.S. Pat. No. 7,838,044) teaches the extraction of sweet glycosides from the Stevia rebaudiana Bertoni in the presence of pectinase, and purification by contacting the extract with cyclodextrin and bentonite and ion-exchange resins, followed by crystallization and recrystallization from ethanol. Kutowy et al. (U.S. Pat. No. 5,972,120) disclose a process for the extraction of sweet compounds from Stevia rebaudiana (Bertoni) in a vertical extraction column, followed by purification by filtration, by using microfiltration as a pre-treatment step to clarify the extract, then ultrafiltration followed by nanofiltration. Payzant et al. (U.S. Pat. No. 5,962,678) uses two ion exchange columns to remove impurities from sweet glycosides extracted from the Stevia rebaudiana, methanol being used to elute sweet glycosides from the second column, and cooling the solution to crystallize Stevioside. The filtrate is further concentrated and cooled to crystallize out Rebaudioside A.

U.S. Pat. No. 4,612,942 discloses diterpene glycosides, including Rebaudioside D, and their use in foodstuffs, medical compositions, oral hygiene compositions, chewing compositions and smoking compositions.

It has been determined that some of these undesirable properties can be reduced or eliminated by subjecting steviol glycosides to the reaction of intermolecular transglucosylation, when new carbohydrate residues are attached to initial molecule at $C_{13}$ and $C_{19}$ positions. Depending on the number of carbohydrate residues in these positions the quality and potency of the compounds taste will vary. Table 1 illustrates how sweetness quality and intensity vary with the number and position of glycosides. Glucose moieties (designated as Glue or G in the table) are connected by a beta-glycosidic linkage. Pullulanase, isomaltase (Lobov S. V. et al. (1991) Enzymatic production of sweet stevioside derivatives: transglycosylation by glucosidases. Agric. Biol. Chem. 55: 2959-2965), 3-galactosidase (Kitahata S. et al. (1989) Production of rubusoside derivatives by transglycosylation of various β-galactosidase. Agric. Biol. Chem. 53: 2923-2928), and dextran saccharase (Yamamoto K. et al. (1994) Effective production of glucosyl-stevioside by α-1, 6-transglucosylation of dextran dextranase. Biosci. Biotech. Biochem. 58: 1657-1661) have been used as transglycosylating enzymes, together with pullulan, maltose, lactose, and partially hydrolyzed starch, respectively, as donors of glycosidic residues to extend linearly the carbohydrate portion on the steviol glycoside core with alpha-linked glucose units.

The transglucosylation of steviol glycosides was also performed by action of cyclodextrin glucanotransferases (CGTase) produced by Bacillus stearothermophilus (U.S. Pat. Nos. 4,219,571, and 7,807,206). As a result, α-1,4-glucosyl derivatives were formed with a degree of polymerization up to 10.

It was shown that the taste profile and sweetness power of glucosyl derivatives are largely dependent on a number of additional glucosyl derivatives, i.e., the degree of polymerization of the α-1,4-glucosyl chain. The increase in number of α-1,4-glucosyl residues improved the taste quality but at the same time reduced the sweetness level. (Tanaka, 1987).

It is to be noted also that many glucosyl Stevia products contain up to 20% residual dextrins which do not possess significant functional properties and reduce the content of steviol glycosides in the product, further reducing sweetness intensity.

Therefore, it is necessary to develop a simple and efficient process of preparation of high purity Stevia glycosides.

China Published Application No. CN103012516 to Wuxi Kingboon Stevia Internat Trade Co. Ltd. discloses methods of preparing stevioside that include a step of soaking Stevia leaves in water; a step of coarse filtration and ultrafiltration to obtain an ultrafiltration solution; a step of introduction of the ultrafiltration solution to a nano micro guard column; and at least two steps of alcoholysis on the nano micro guard column.

China Published Application No. CN102127129 to Liaoning Qianqian Biolog Technology Co. discloses a method of preparing a Stevia extract that includes a step of mechanical crushing Stevia leaves; a step of filtering the Stevia leaves; a step of ultrasonic extraction; a step of flocculation; a step of adsorption; a step of analysis via ethanol elution; a step of desalting and decolorizing; a step of concentrating; and a step of spray drying.

China Published Application No. CN102406113 to Ningbo Green Health Pharmaceutical Co. Ltd. discloses a method to prepare a rebaudioside A/rebaudioside D preparation that includes a step of extracting pulverized Stevia leaves with water; a step of passing the filtrate through a macroporous resin column; and a step of eluting with an alcoholic solvent using HPLC analysis detecting rebaudioside A/rebaudioside D content.

U.S. Published Application No. 20130071537 to E.P.C Plant Pharmaceutical Technology Co., Ltd. discloses compositions of Stevia based sweeteners that include a salt form of Rebaudioside B.

U.S. Published Application No. 20140243514 to Cargill, Incorporated discloses a method of preparing an enriched composition comprising at least one of rebaudioside B, rebaudioside D, or a mixture thereof that includes use of a macroporous neutral porous resin.

U.S. Published Application No. 20130309389 to Cargill, Incorporated discloses a composition that contains specified amounts of rebaudioside D and rebaudioside B.

U.S. Published Application No. 20140004248 to LGL Life Tech Corporation discloses a process for producing a natural sweetener composition comprising at least one of steviolbioside extract, rebaudioside B extract and rebaudioside D extract, comprising the use of a porous adsorption column having specified parameters. U.S. Published Application No. 20130071339 to Markosyan discloses methods of preparing highly purified steviol glycosides, particularly Rebaudioside D.

U.S. Published Application No. 20150017284 to Markosyan discloses a rebaudioside M and rebaudioside D crystalline composition containing at least 75% rebaudioside M.

U.S. Published Application No. 20130071339 to Markosyan discloses a method for purifying steviol glycosides that includes the use of consecutively connected columns packed with an adsorbent resin capable of adsorbing steviol glycosides.

U.S. Pat. No. 8,299,224 to PureCircle Sdn Bhd discloses a method for purifying Rebaudioside D from Stevia extract that includes providing an extract of Stevia; dissolving the extract in a first aqueous solution of organic solvent to result in a first mixture of steviol glycosides, wherein the organic solvent is selected from the group consisting of methanol, ethanol, 1-propanol, isopropanol, and a mixture thereof, and the organic solvent is 75-99 vol. %; inducing crystallization in the first mixture; filtering the mixture from to obtain a first precipitate and a first filtrate; dissolving the first precipitate in a second aqueous solution of organic solvent to result in a second mixture, wherein the organic solvent is selected from the group consisting of methanol, ethanol, 1-propanol, isopropanol, and a mixture thereof, and the organic solvent is 70-80-vol. %; inducing crystallization in the second mixture; filtering the mixture to obtain a second precipitate and a second filtrate; dissolving the second precipitate in a third aqueous solution of organic solvent to result in a third mixture, wherein the organic solvent is selected from the group consisting of methanol, ethanol, 1-propanol, isopropanol, and a mixture thereof, and the organic solvent is 10-80 vol. %; inducing crystallization in the third mixture; and filtering the mixture to obtain a third precipitate and a third filtrate; whereby drying the third precipitate yields purified Rebaudioside D.

U.S. Published Applications Nos. 20140335253, 20140335254, 20140335264 and 20140335265 to EPC Beijing Natural Products Co. Ltd. disclose non-natural rebaudioside D compositions that contain an increased amount of purified rebaudioside D, wherein the increased amount of purified rebaudioside D is added as purified rebaudioside D to the compositions.

U.S. Published Application No. 20120269954 to Tate & Lyle Ingredients Americas LLC discloses a Stevia extract comprising Rebaudioside B.

U.S. Published Application No. 20110256588 to Lee et al. discloses a method of producing Rebaudioside A in a high yield by recycling by-products produced when Rebaudioside A is produced from leaves of Stevia Rebaudiana Bertoni.

U.S. Published Application No. 20110183056 to Morita et al. discloses isolated steviol glycosides having the structures disclosed therein. The reference discloses that the steviol glycosides, which have structures which present more glycosidic moieties than on stevioside or Rebaudioside A, may provide a subtle improvement to Stevia sweetener taste.

U.S. Pat. No. 8,520,527 to PureCircle Sdn Bhd discloses a process for producing a Stevia food ingredient that includes a step of soaking a Stevia biomass in water to remove soluble components; a step of incubating a water-insoluble Stevia biomass in alkaline solution to produce a pulp; and further processing steps to achieve a Stevia food ingredient that contains microcrystalline cellulose.

U.S. Pat. No. 8,337,928 to Concentrate Manufacturing Company of Ireland discloses a beverage product that comprises at least one steviol glycoside sweetener and anisic acid.

U.S. Pat. Nos. 8,318,459 and 8,257,948 to PureCircle USA disclose a process for producing a highly purified glucosyl Stevia composition using starch as a source of the glucose residues.

U.S. Pat. No. 8,299,224 to PureCircle Sdn Bhd discloses a method for purifying Rebaudioside D from Stevia extract.

U.S. Pat. No. 8,277,862 to Concentrate Manufacturing Company of Ireland discloses a beverage product that comprises Rebaudioside A, erythritol and an acid component.

U.S. Pat. No. 8,277,862 to Concentrate Manufacturing Company of Ireland discloses a beverage product that comprises a steviol glycoside and an acid component.

U.S. Pat. No. 7,964,232 to PepsiCo, Inc. discloses steviol glycoside isomers wherein the exo-cyclic double bond of formula I therein has been moved to an endo-cyclic position within the five-membered ring.

U.S. Pat. No. 7,927,851 to Vineland Research and Innovation Centre discloses a method of producing a steviol glycoside in a plant or plant cell comprising, a) selecting a plant or plant cell that produces ent-kaurenoic acid; b) transforming the plant or plant cell with a first nucleotide sequence encoding a polypeptide having ent-kaurenoic acid 13-hydroxylase activity, and at least one other nucleotide sequence encoding one or more glucosyltransferases to catalyse the addition of one or more glucose molecules to steviol, or glucosyl-steviol; and c) expressing the polypeptide having ent-kaurenoic acid 13-hydroxylase and said one or more glucosyltransferases in the cell to convert ent-kaurenoic acid to one or more steviol glycosides.

Ohta et al., Characterization of novel steviol glycosides from leaves of Stevia rebaudiana morita, J. Appl. Glycosci., 57, 199-209 (2010), discloses the structures of steviol glycosides extracted from leaves of S. rebaudiana Morita, which was produced by selection and breeding of S. rebaudiana Bertoni.

Zimmerman, Tandem mass spectrometric fragmentation patterns of known and new steviol glycosides with structure proposals, Rapid Commun. Mass. Spectrom. 2011, 25, 1575-1582, discloses the use of tandem mass spectrometry to identify 12 previously unknown steviol glycosides.

Brandle et al. (2002) Plant Molecular Biology 50: 613-622; Richman et al. (1999) The Plant Journal 19(4), 411-421; and Richman et al., (2005) The Plant Journal 41, 55-67, disclose metabolic pathways for the production of steviol and the conversion of steviol to various steviol glycosides.

Existing methods deal with isolation and purification of a steviol glycoside from an initial extract and do not show a way for the further treatment of residual solution or purification of minor compounds, individually or collectively. Thus, there remains a need for an efficient and economical method for comprehensive retreatment of extract produced from Stevia rebaudiana plants.

SUMMARY OF THE INVENTION

The invention relates to a comprehensive process for separation, isolation, characterization and use of two or more minor steviol glycosides (and, in particular, those naturally occurring at less than 1% dry leaf weight) from *Stevia rebaudiana* plants.

According to an embodiment, an efficient method of separating, isolating and characterizing combinations of two or more steviol glycosides from *Stevia* extract is provided, thus minimizing waste.

The combinations of two or more steviol glycosides, alone or in the combination with other sweeteners and/or other ingredients, are useful as non-caloric sweeteners in edible and chewable compositions such as beverages, confectionaries, bakeries, cookies, chewing gums, pharmaceuticals and the like.

According to an embodiment, the method includes:
1. the use of a chromatographic method for the identification and quantitation of combinations of two or more minor steviol glycosides (occurring at less than 5% dry leaf weight) as a means of informing a breeding program to optimize for the production of that defined set of steviol glycosides, which are not currently used commercially as sweeteners,
2. the method of extracting, including by staged extraction, of *Stevia* leaves, fresh leaves or desiccated for preservation, to optimize recovery of the two or more minor steviol glycosides of molecular weight greater than about 900 g/mol, and minimize the need for subsequent processing steps,
3. the use of chromatography to isolate a collection of two or more steviol glycosides of molecular weight greater than about 900 g/mol, preferably rebaudiosides D, I, O M and/or N, all of which individually occur at levels below 5% dry leaf weight basis,
4. a process which avoids the need for crystallization in the isolation of steviol glycosides D, I, O M and/or N, which involves gradient elution using 2 or more solvents at a constant temperature, or at a temperature gradient with the eluting solvent,
5. the use as a sweetener of a combination of two or more steviol glycosides, preferably rebaudiosides D, I O, M and/or N, which individually occur at levels below 5% dry leaf weight basis,
6. the two or more steviol glycosides can be used alone or in combination with more predominant steviol glycosides, including, but not limited to, Rebaudioside A, Rebaudioside B, Rebaudioside D, in amounts less than about 25% predominant steviol glycoside, less than about 15% predominant steviol glycoside, less than about 10% predominant steviol glycoside, less than about 5% predominant steviol glycoside. Table 9, taken from Ohta et al. (2010), provides the relative amounts of steviol glycosides from the leaves of *S. rebaudiana* Morita and *S. rebaudiana* Bertoni.

Continuous counter current ion exchange and adsorption such as SepTor technology by Outotec, Espoo, Finland, is a technique that could be employed to remove contaminants. Continuous chromatography is different from conventional (single or multi-column) stationary solid phase chromatography in that the multiple columns employed in continuous chromatography are operated as if they were a single column, but with multiple feed points and discharge points between the columns to enable progressively advancing the feed points for the mixture and eluting solvent, and the take-off points for faster and slower eluting components in the mixture. This mode of operation allows each component column segment to be operated autonomously with respect to eluant composition or flow rate. The simulation of continuous separations process is described by Johan Samuelsson in "Simulation of continuous chromatographic processes" and by Niklas Andersson in "Simulation of continuous preparative chromatography: A case study in MCSGP." (2009) for the use of a solvent gradient (SG) in a multi column (MC) system. "Preparative" (P) relates to effecting a separation at a scale larger than for analytical purposes, up to commercial production scale. The application of continuous chromatographic separation of sugars is well developed in the beet sugar refining industry and is described by Bubnik and co-authors in "Application of continuous chromatographic separation in sugar processing", Journal of Food Engineering 61 (2004) 509-513. The application of continuous separation methods must be customized to the type of separation undertaken. For example, a separation strategy for the isolation of high purity rebaudioside A will be different from the operation of the system for a custom mixture of other steviol glycosides. Up to the present, continuous separation methods have not been applied to the isolation of custom steviol glycoside mixtures comprising at least two steviol glycosides selected from rebaudiosides A, D, I, O, M, and N.

Another important distinction in continuous chromatography is the use of a persistent inventory of material to be separated residing in the multi-column system and which is continually circulated in the system. This inventory is advantageously employed in aiding the separation by adjusting the inventory of individual components to favor a desired composition. For example, if a feed mixture has a low level of a set of desired components (e.g., 3-5% rebaudiosides A, D, I, O, M, and N) but a dominant portion (>20%) of rebaudioside A, the column can be operated initially by taking off mainly the predominant component while allowing the lesser components to remain inventory in the column. This may allow the lesser components in the feed to be better resolved in the column inventory from other components enabling the take-off of a stream enriched in the desired (minor) components.

The ability to operate each column independently is of crucial importance in separations involving two or more inputs to the separation system (e.g., process feed, eluent A and eluent B), and two or more take-offs (e.g., Product 1, Product 2, Product 3, etc.) where the flow rates of take-off are different for each. The column flow balance is calculated as $$F_{in(preceding\ column)} + F_{in(feed)} = F_{out(Product)} + F_{out(to\ next\ column)}$$

Where $F_{in(feed)}$ may be the process feed or an eluting solvent and $F_{out(product)}$ is a product take-off.

Simulated Moving Bed

In manufacturing, the simulated moving bed (SMB) process is a highly engineered process for implementing chromatographic separation. It is used to separate one chemical compound or one class of chemical compounds from one or more other chemical compounds to provide significant quanitites of the purified or enriched material at a lower cost than could be obtained using simple (batch) chromatography. It cannot provide any separation or purification that cannot be done by a simple column purification. The process is rather complicated. An advantage that it brings to a chromatographic purification is that it allows the production of large quantities of highly purified material at a dramatically reduced cost. The cost reductions come about as a result of: the use of a smaller amount of chromatographic separation media stationary phase, a continuous and high rate of production, and decreased solvent and energy requirements. This improved economic performance is brought about by a valve-and-column arrangement that is used to lengthen the stationary phase indefinitely and allow very high solute loadings to the process.

In the conventional moving bed technique of production chromatography the feed entry and the analyte recovery are simultaneous and continuous, but because of practical difficulties with a continuously moving bed, simulated moving bed technique was proposed. In the simulated moving bed technique instead of moving the bed, the feed inlet, the solvent or eluent inlet and the desired product exit and undesired product exit positions are moved continuously, giving the impression of a moving bed, with continuous flow of solid particles and continuous flow of liquid in the opposite direction of the solid particles.

Another form of continuous chromatographic separation is annular chromatography. In a published review, Frank Hilbrig and Ruth Freitag ("Continuous annular chromatography", Journal of Chromatography B, 790 (2003) 1-15) report "The principle of continuous annular chromatography (CAC) has been known for several decades. CAC is a continuous chromatographic mode, which lends itself to the separation of multi-component mixtures as well as of bi-component ones. In CAC, the mobile and stationary phases move in a crosscurrent fashion, which allows transformation of the typical one-dimensional batch column separation into a continuous two-dimensional one. With the exception of linear gradient elution, all chromatographic modes have at present been applied in CAC." Earlier, Bart and co-authors (Continuous chromatographic separation of fructose, mannitol and sorbitol. Chemical Engineering and Processing 35 (1996) 459-471) applied the method to separation of simple sugars, but this method has not been employed for the separation of steviol glycosides.

Figure 1:
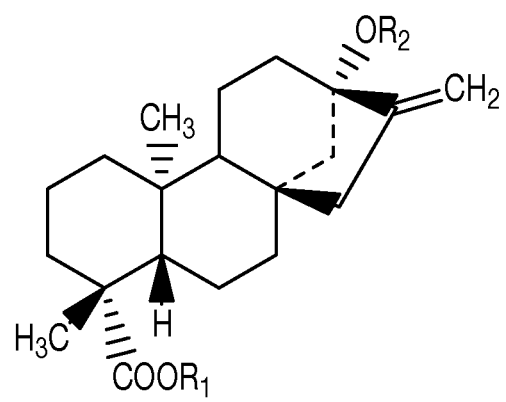
FIG. 1 shows steviol glycoside aglycone structure with indicated location of glycosylation (R1 and R2).

The present invention may be more fully understood by reference to the Figures, Detailed Description and Examples which follow.

DETAILED DESCRIPTION OF THE INVENTION

It is believed that one skilled in the art can, based upon the description herein, utilize the present invention to its fullest extent. The following specific embodiments are to be construed as merely illustrative, and not as limiting the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified. In addition, all ranges set forth herein are meant to include any combinations of values between the two endpoints, inclusively.

Definitions

By the term "flavor notes" it is meant subtle sensory aspects typically detected by taste, or smell experienced while exhaling through the nose after ingestion (retronasal olfaction).

By the term "steviol" it is meant the diterpenoic compound hydroxy-ent-kaur-16-en-13-ol-19-oic acid, which is the hydroxylated form of the compound termed "ent-kaurenoic acid", which is ent-kaur-16-en-19-oic acid.

By the term "steviol glycoside" it is meant any of the glycosides of the aglycone steviol including, but not limited to, stevioside, Rebaudioside A, Rebaudioside B, Rebaudioside C, Rebaudioside D, Rebaudisode E, Rebaudisode F, Rebaudioside I, Rebaudiouside M, Rebaudioside N, Rebaudioside O, dulcoside, rubusoside, steviolmonoside, steviolbioside, and 19-O-β-glucopyranosyl-steviol.

Examples of synthetic sweeteners include sucralose, potassium acesulfame, aspartame, alitame, saccharin, neohesperidin dihydrochalcone synthetic derivatives, cyclamate, neotame, dulcin, suosan, N—[N-[3-(3-hydroxy-4-methoxyphenyl)propyl]-L-α-aspartyl]-L-phenylalanine 1-methyl ester (Advantame), N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and the like.

Examples of natural high intensity sweeteners include Stevioside, Rebaudioside A, Rebaudioside B, Rebaudioside C, Rebaudioside E, Rebaudioside F, Steviolbioside, Dulcoside A, Rubusoside, some mogrosides (for example, Mogroside V), brazzein, neohesperidin dihydrochalcone (NHDC), glycyrrhizic acid and its salts, thaumatin, perillartine, pernandulcin, mukuroziosides, baiyunoside, phlomisoside-I, dimethyl-hexahydrofluorene-dicarboxylic acid, abrusosides, periandrin, carnosiflosides, cyclocarioside, pterocaryosides, polypodoside A, brazilin, hernandulcin, phillodulcin, glycyphyllin, phlorizin, trilobatin, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, siamenoside and others.

Suitable "heat-stable, high-intensity sweeteners" include chemical compounds or mixtures of compounds, which elicit a sweet taste at least five times sweeter than sucrose, as measured in accordance with the test method described in G.B. Patent No. 1,543,167, which is incorporated by reference herein. Typically such sweeteners are substantially free from degradants after being heated for about one hour at about 40° C. Examples of such suitable sweeteners include, but are not limited to, sucralose, neotame, saccharin, acesulfame-K, cyclamate, neohesperdine DC, Stevia, thavmatin, brazzein, aspartame, and mixtures thereof.

Stevia is a non-caloric natural sweetener from the plant Stevia rebaudiana. The plant makes a number of sweet compounds collectively referred to as steviol glycosides, which make Stevia up to 300 times sweeter than sucrose. These glycosides can be extracted from the plant with water and other solvents well known to those skilled in the art. They are heat stable, pH stable, do not ferment, and do not induce a glycemic response.

Stevioside, sometimes referred to as 13-[(2-O-β-D-glucopyranosyl-α-D-glucopyranosyl)oxy]-kaur-16-en-18-oic acid β-D-glucopyranosyl ester, and rebaudioside A are exemplary glycosides of the diterpene derivative steviol, extracted and refined from Stevia rebaudiana (also known as Eupatorium rebaudianum) leaves. These glycosides are high intensity sweeteners, about 100 to about 500 times that of sucrose, but have metallic and bitter notes. They can be used in a wide range of low or reduced calorie food products and beverages.

Other sweet glycosides can also be extracted from Stevia rebaudiana. These have varying degrees of sweetness. As used herein "Stevia extract" means a sweet glycoside extracted from a Stevia plant.

Of the glycosides found in Stevia extracts, Rebaudioside A has been generally believed to have the least aftertaste. This aftertaste, which has been described by many as bitter and licorice like, is present in all current Stevia-sweetened products. Such formulations typically require extensive dilution or taste-masking technology.

Like with all high intensity sweetener containing sweetener compositions, Stevia containing sweetener compositions typically have been provided with a bulking agent to aid in measurement and distribution into the users application. Among those disclosed or used include fructooligosaccharide (FOS) and other fibers, maltodextrins, and erythritol. Erythritol is especially popular as it can mitigate some of the bitter taste.

U.S. Patent Applications Nos. 20120201952 and 20120201940 to Catani et al. disclose a method of making a natural sweetening composition comprising steam stripping a crude mixture comprising at least one plant based natural high intensity sweetening compound and filtering the crude mixture.

U.S. Application Serial No. 20100285201 to Catani et al. discloses a synergistic sweetening composition that comprises sucralose and a purified extract of Stevia, wherein the purified extract of Stevia comprises rebaudiosides and dulcosides.

U.S. Patent Application No. 20090017185 to Catani et al. discloses a reduced calorie sweetening composition consisting of a Stevia extract and a simple sugar. The reference discloses that the Stevia extract may have a rebaudioside A level of from about 80 wt % to about 99.5 wt % relative to all steviol glycosides and the simple sugar may be sucrose, fructose or glucose.

U.S. Patent Application No. 20090004355 to Catani discloses a sweetening composition comprising erythritol and a Stevia extract.

The present invention provides a process for the separation, isolation and characterization of a combination of two or more sweet glycosides from Stevia rebaudiana plant extract with molecular weights in the range of about 966 g/mol to about 1436 g/mol and with Rebaudioside A less than 25% of steviol glycosides, more preferably with Rebaudioside A less than 15% of steviol glycosides, more preferably with Rebaudioside A less than 10% of steviol glycosides, and more preferably with Rebaudioside A less than 5% of steviol glycosides.

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Among sweet glycosides existing in Stevia, only Stevioside, Rebaudioside A and Rebaudioside C are available at moderate cost at <80% purity and at high cost at >80% purity. The highest purity of commercial product usually is more than 97%. Hereinafter, the term "highly purified" refers to a steviol glycoside composition that includes at least about 90% to about 100% of the steviol glycoside on a dry weight basis. In the market there are no commercial quantities of highly purified Rebaudioside B or Rebaudioside D, two Stevia components with taste quality and intensity comparable to Rebaudioside A. Rebaudiosides E and F, also good-tasting sweeteners, are available in minor quantities as analytical standards. No commercial use has been made of naturally occurring steviol glycosides of molecular mass comparable or larger than Rebaudioside D. The present invention seeks to define a composition of such large molecular mass components, and low-cost method of obtaining that composition, which compensates for the low concentration of the components in Stevia rebaudiana by using them collectively as a sweetening agent.

There is a need for an efficient and economical method for comprehensive separation, isolation and/or characterization of combinations of two or more sweet glycosides from Stevia extract with molecular weight greater than about 900 g/mol. Individual steviol glycosides that have been developed for commercial use have limitations in terms of taste quality and sweetness temporal profile. The characteristics and limitations of isolated naturally occurring and man-made sweeteners is described by Grant E. DuBois and Indra Prakash in *Annu. Rev. Food Sci. Technol.* (2012), 3:353-380 (Non-Caloric Sweeteners, Sweetness Modulators, and Sweetener Enhancers). The present invention eschews the concept of isolation of individual sweet components in favor of separation, isolation and/or characterization of a combination of two or more molecules from Stevia.

EXAMPLES

Figure 2:
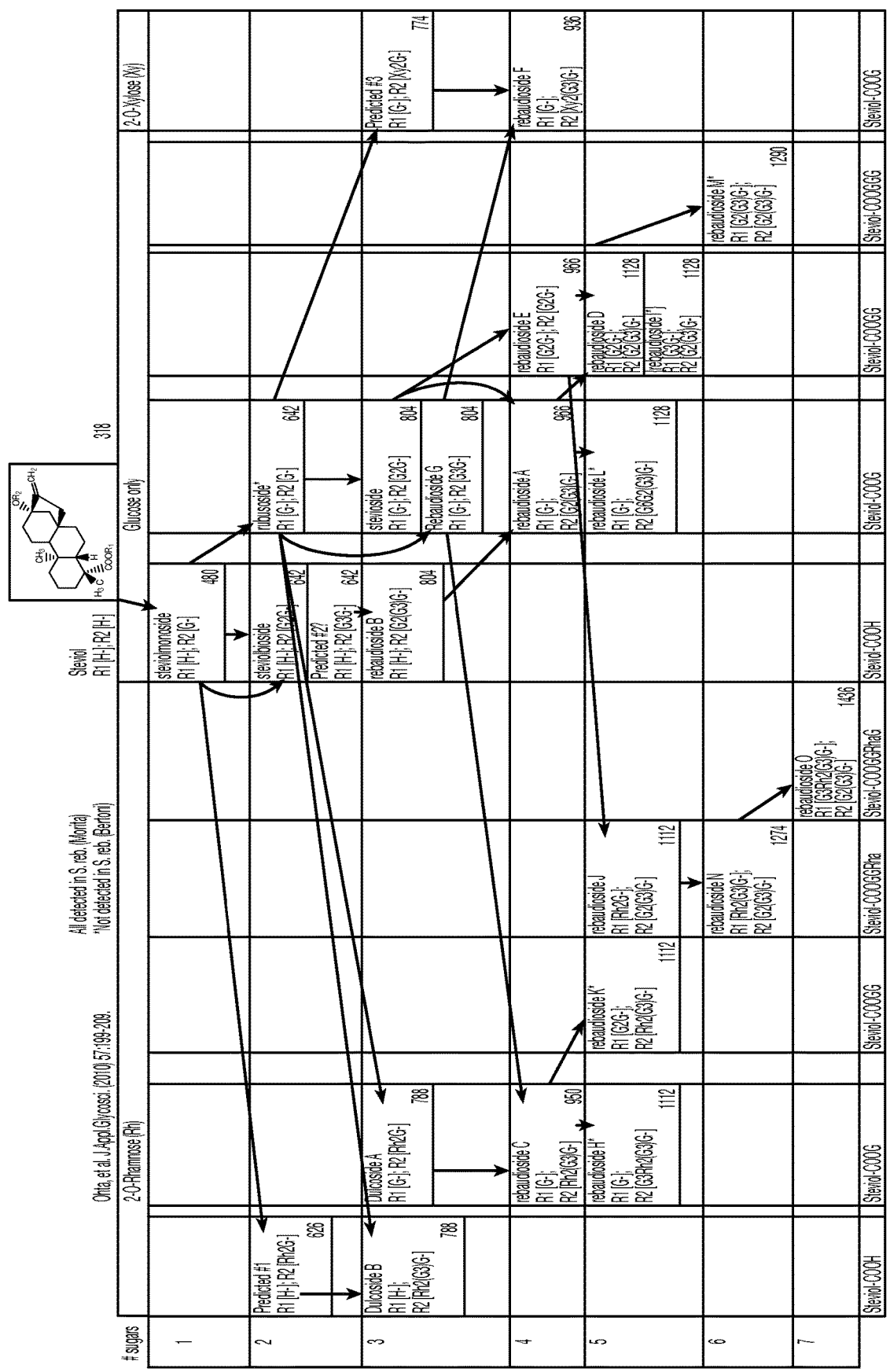
FIG. 2 shows the organization of steviol glycosides.

The known steviol glycosides can be ordered on the basis of the sugar (glycoside) substitution pattern. This allows for the prediction of other missing or as yet unidentified steviol glycosides that may be present, albeit at very low levels in various preparations. The organization of steviol glycosides is illustrated in FIG. 2.

Figure 3:
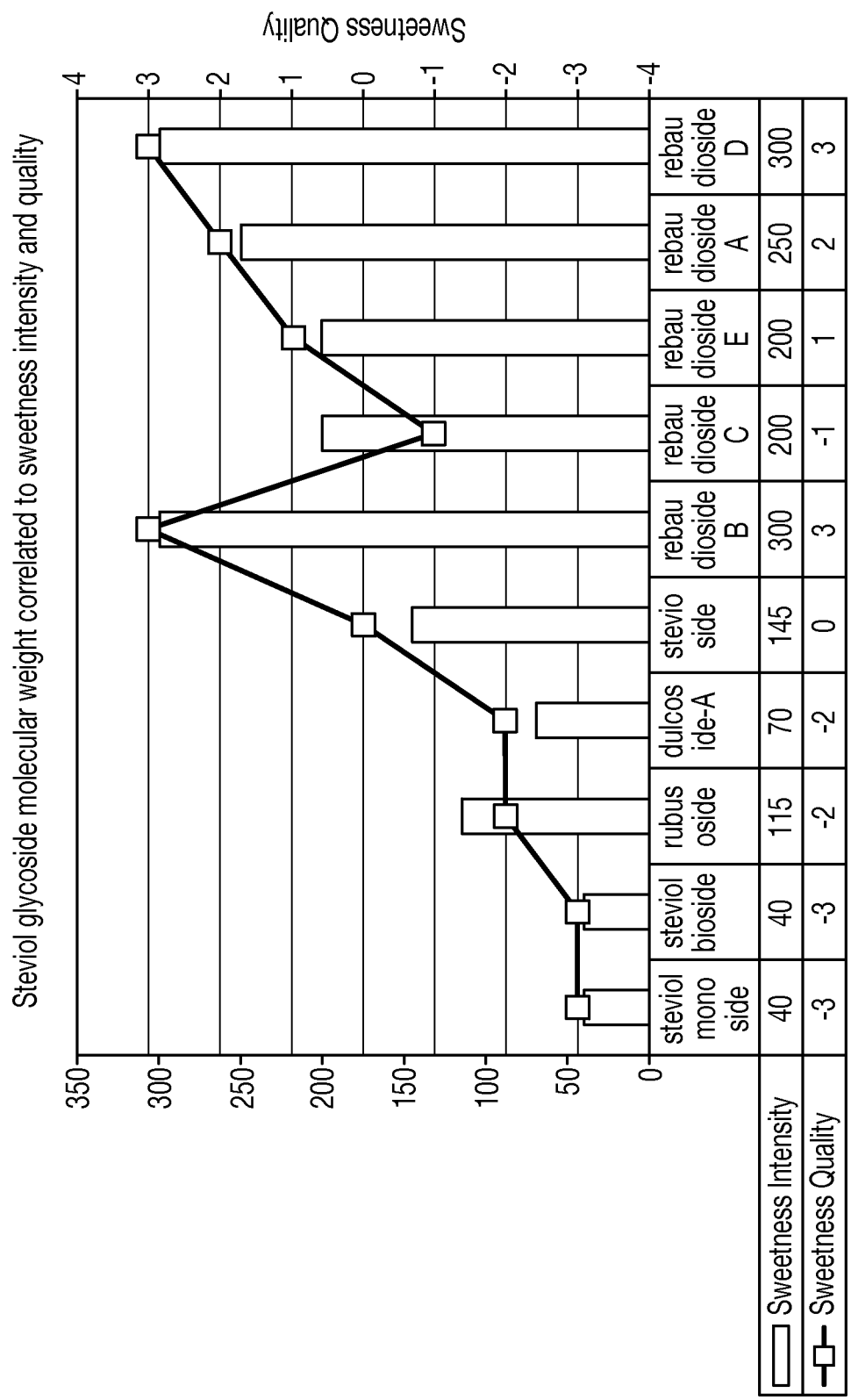
FIG. 3 is a chart that how subjective taste quality and sweetness can be predicted by molecular size of the steviol glycoside.

The sweetness quality and intensity of steviol glycosides is found to be correlated with the extent of glycosylation on the steviol aglycone. FIG. 3 below illustrates how subjective taste quality and sweetness can be predicted by molecular size, although exceptions may occur, such as rebaudioside B. This compound may be illustrative of the importance of the specific glycoside structure at R2, even in the absence of glycosylation at R1, in defining sweetness quality and intensity.

Sweetness quality and intensity is also affected by the presence of monosaccharides other than glucose. Thus, the presence of rhamnose (Rh) in the molecule, such as in dulcoside A or rebaudioside C, results in a lesser sweetness intensity and quality relative to steviol glycosides substituted with the same number of glucose-only monosaccharides, such as stevioside or rebaudioside A, respectively.

TABLE 1

Steviol glycoside glycosylation pattern correlates with sweetness.

| Steviol glycoside | R1 | R2 | #Glucose (G) | #Rhamnose (Rh) | Mol. Wt. | Sweetness Intensity | Sweetness Quality |
|---|---|---|---|---|---|---|---|
| steviol | | | | | 318 | | |
| steviolmonoside | | G- | 1 | | 480 | 40 | −3 |
| steviolbioside | | G-2G- | 2 | | 642 | 40 | −3 |
| rubusoside | G- | G- | 2 | | 642 | 115 | −2 |
| dulcoside-A | G- | Rh2-G- | 2 | 1 | 788 | 70 | −2 |
| stevioside | G- | G2-G- | 3 | | 804 | 145 | 0 |
| rebaudioside B | | G2-(G3)-G- | 3 | | 804 | 300 | 3 |
| rebaudioside-C | G- | Rh2-(G3)-G- | 3 | 1 | 950 | 200 | −1 |
| rebaudioside-E | G2-G- | G2-G- | 4 | | 966 | 200 | 1 |
| rebaudioside-A | G- | G3-(G2-)G- | 4 | | 966 | 250 | 2 |
| rebaudioside-D | G2-G- | G2-(G3)G- | 5 | | 1128 | 300 | 3 |

Note:
Sweetness quality and intensity data from Osamu Tanaka. "Improvement of taste of natural sweeteners". Pure & Appl. Chem. 1997, 69(4), 675-683. Sweetness intensity is understood to be relative to an equal weight of sucrose. Sweetness quality is a subjective relative ranking.

Steviol glycosides differ from each other not only by molecular structure, but also by their taste properties. Usually stevioside is found to be about 110 to about 270 times sweeter than sucrose, Rebaudioside A is between about 150 and about 320 times, and Rebaudioside C is between about 40 and about 60 times sweeter than sucrose. Dulcoside A is about 30 times sweeter than sucrose. Sweetness intensity is known to vary somewhat with temperature and viscosity of the carrier medium.

While several steviol glycosides are now known, not all have been evaluated for sweetness quality and intensity. Also, while many processes are employed to isolate and exploit individual steviol glycosides as sweeteners, current knowledge does not permit predicting sweetness characteristics of steviol glycoside blends, particularly in proportions other than that found naturally, or of taste characteristics when combined with other sweeteners, whether caloric or non-caloric, of high intensity or more commensurate with simple mono- and disaccharides like glucose, fructose or sucrose.

Method of Analysis

Conventional methods of analysis of steviol glycosides require dual solvent gradients to separate steviol glycosides from other non-sweet plant extract components. Consequently, detectors that use refractive index changes in the eluent are not useful. Typically, ultraviolet (UV) detectors are employed to assay steviol glycosides which contain a weak UV chromophore. This method is of limited usefulness to assay crude extracts because of the presence of components with stronger chromophores which obscure the detection of the components of interest because components with a large molar extinction coefficients at the wavelength selected will appear more prominent than components with lower extinction coefficients, which though present at a higher concentration on a mass basis, will produce a much weaker signal. Another alternative to refractive index (RI) for mass-based detection include evaporative light scattering (ELS) and charged aerosol detection (CAD). THERMO Scientific (Determination of Steviol Glycosides by HPLC with UV and ELS Detections. Application Note 241 (2012)) teaches how ELS can present advantages over UV detection in measuring the content of Rebaudioside A and Stevioside in table-top sweetener formulations. However, in our experience, ELS can be of limited use in measuring the concentration of a minor component in the presence of another closely eluting major component. H. Y. Eom et al. (J. Chromatogr. A 1217 (2010) 4347-4354) teach that the detection of saponins derived from the roots of *Bupleurum falcatum* L. (Umbelliferae) is more sensitive with CAD than with ELS. We have found that using a charged aerosol detector, ESA®, Inc., Chelmsford, Mass., allows for good quantitation of steviol glycosides in crude extracts of *Stevia rebaudiana*, which preparations are rich in proteins and other plant components that have strong UV absorbance, and also in the presence of larger amounts of polysaccharides or other steviol glycosides which can "blind" the detector to lower levels of the components of interest.

Identification of an effective detector is only part of the system for effective quantitation of the components of interest in a crude preparation. Another part of the system is identification of a solvent system (mobile phase) and solid support (stationary phase) to accomplish the separation. The successful development of a suitable combination of mobile and stationary phases is an empirical process of trial and error which is not predictable a priori. We have experimented with various gradient system mobile phase systems to discover a solvent gradients that useful to separate the steviol glycosides of interest, thus enable their identification by mass spectrometry, and quantitation by CAD. An example is shown below. The gradient can be adjusted to allow greater resolution around a particular peak region such as near Rebaudioside D.

Chromatographic Method of Analysis:
Stationary phase: Phenomenex Kinetex C-18, 150×4.6, 2.6 µm; Column temp.: 55° C.;
Injection Volume is 10 µL.
Mobile phase (MPA and MPB; flow rate: 0.35 mL/min):
MPA: 0.1% formic acid in water
MPB: 0.1% formic acid in acetonitrile

TABLE 2

| Time (minutes) | % A | % B |
|---|---|---|
| 0 | 95 | 5 |
| 5 | 95 | 5 |
| 30 | 70 | 30 |
| 45 | 30 | 70 |

TABLE 2-continued

| Time (minutes) | % A | % B |
|---|---|---|
| 55 | 30 | 70 |
| 55.1 | 95 | 5 |
| 60 | 95 | 5 |

TABLE 3

| Reference identity | RT[1] (min) | Mol. Wt. |
|---|---|---|
| Rebaudioside D | 35.920 | 1128 |
| Rebaudioside A | 39.544 | 966 |
| Stevioside | 39.704 | 804 |
| Rebaudioside F | 40.207 | 936 |
| Rebaudioside C | 40.468 | 950 |
| Rebaudioside A | 40.745 | 788 |
| Rubusoside | 41.474 | 642 |
| Rebaudioside B | 42.027 | 804 |
| Steviolbioside | 42.368 | 642 |
| Steviol | 50.012 | 318 |
| Isosteviol | 52.427 | 318 |

[1]RT—retention time.

Figure 4:
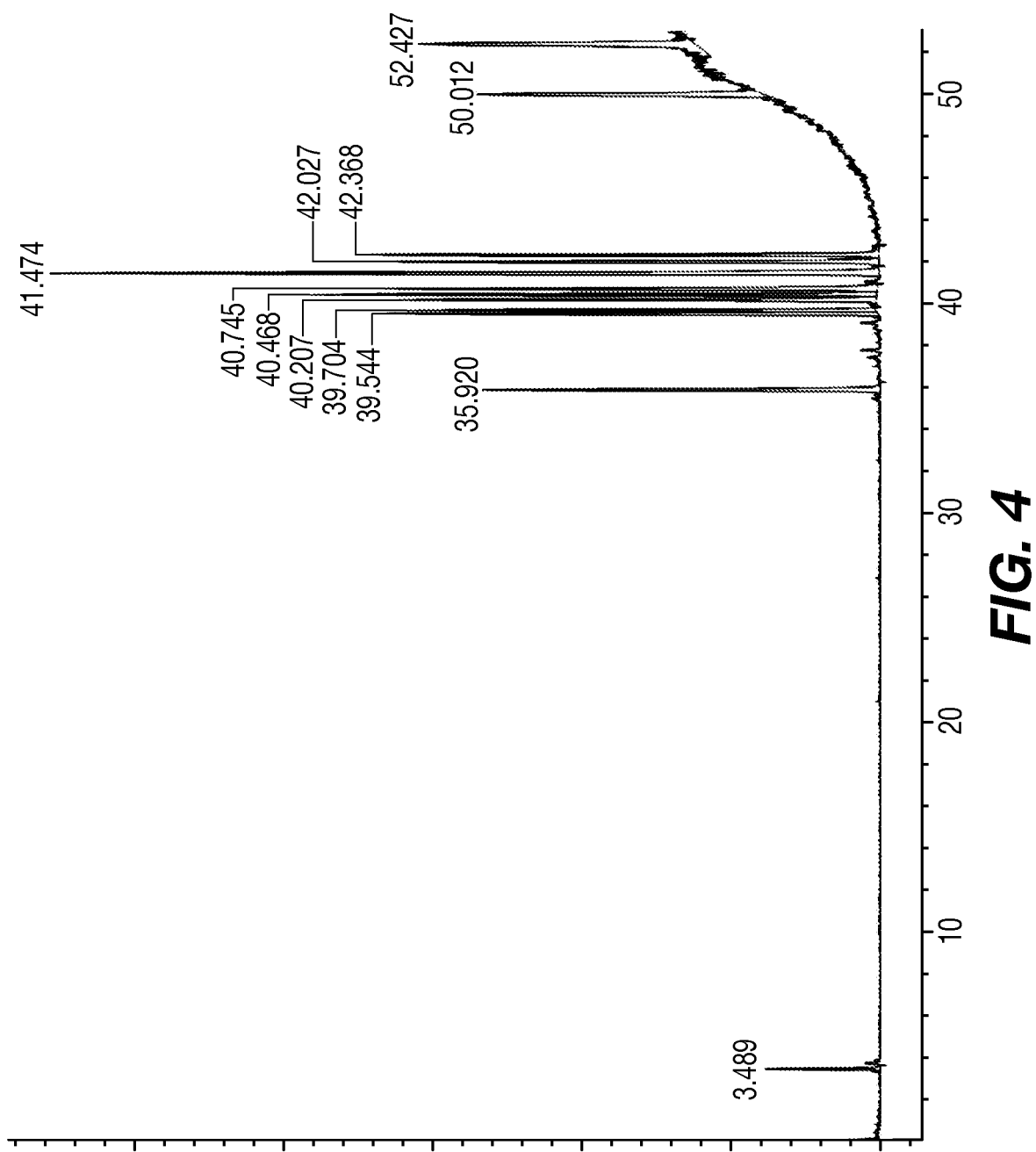
FIG. 4 shows mass spectra for steviol glycosides of interest.

See also FIG. 4.

Figure 5:
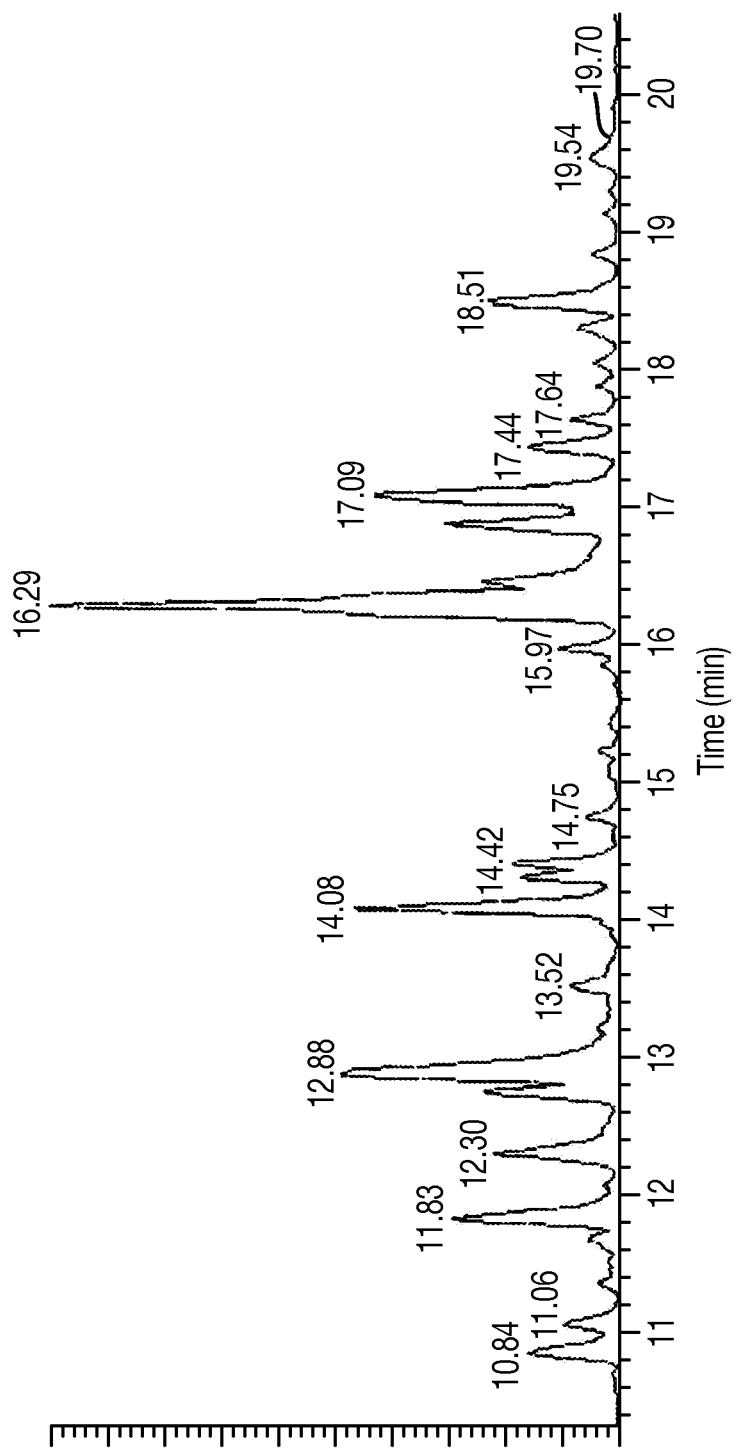
FIG. 5 shows mass spectra for steviol glycosides of interest.
Figure 6:
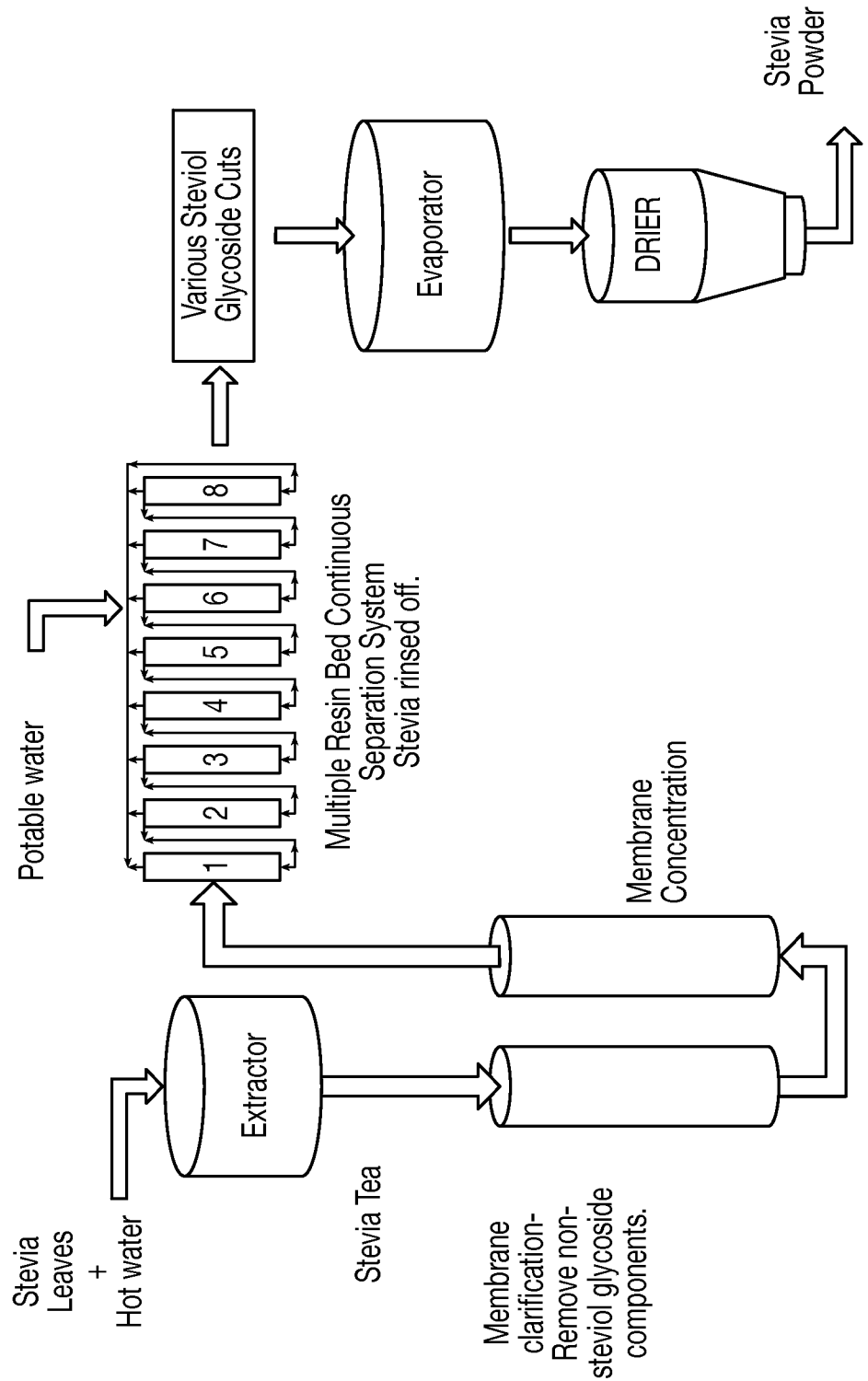
FIG. 6 shows extraction and purification steps that may be used in accordance with the invention.
Figure 7:
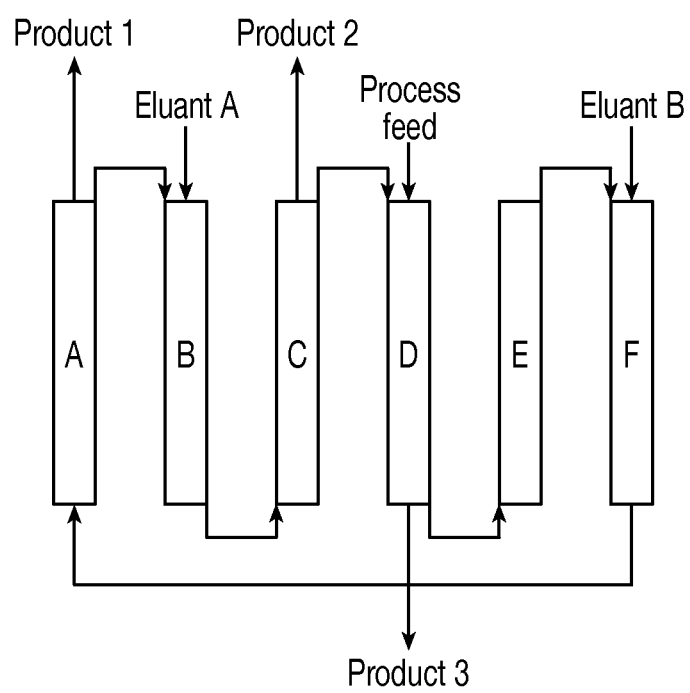
FIG. 7 shows the use of simulated moving bed chromatography in accordance with the invention.

As is known, the gradient can be modified for faster separation (0-2 min 80% MPA, 20% MPB; 2-35 min from 80 to 0% MPA, from 20% to 100% MPB, 35.01-40 min 80% MPA, 20% MPB. Flow rate 0.35 mL/min; injection volume: 5 uL), such as to allow for mass spectrometric identification of steviol glycosides. An example is provided in FIG. 5.

TABLE 4

| Peak identity | RT (min) | Mol. Wt. |
|---|---|---|
| Rebaudioside D | 14.08 | 1128 |
| Rebaudioside N | 14.33 | 1274 |
| Rebaudioside M | 14.42 | 1290 |
| Novel steviol glycoside (possible Reb. O) | 14.75 | Not determined |
| Rebaudioside I | 15.97 | 1128 |
| Rebaudioside A | 16.29 | 966 |
| Stevioside | 16.43 | 804 |

Integration of Analytical Method to Agricultural Development

We have developed a strategy for optimizing the selection of particular breeding progeny of *Stevia* plants based on the steviol glycoside content. It is well known historically that native *Stevia* contained predominantly Stevioside as the main steviol glycoside, but selective breeding has favored the development of progeny in which Rebaudioside A predominates. We have applied our novel analysis to enable identification of breeding progeny that further favor Rebaudioside D or other desirable steviol glycosides with molecular weight (Mol. Wt.) equal or greater than that of Rebaudioside A (Mol. Wt. 966 g/mol), notably Rebaudiosides I, O, M, N, among others that may subsequently be found to occur in new breeding progeny.

Separation of Desirable Steviol Glycosides without Crystallization

We have further developed the insights obtained from the analytical separation of steviol glycosides into a novel process that avoids the need to isolate and purify a single component (typically Rebaudioside A) by crystallization. We have further developed a solvent system which uses food grade ethanol (grain alcohol) and water to separate the steviol glycosides of interest without the need for crystallization.

Example

A crude extract was prepared by subjecting 208.6 g dried leaves to hot water extraction (3 L) for 2 h at 95° C. A portion of the crude extract (100 mL, containing about 1.7 g solids) was directly fractionated on a preparative scale reverse-phase column (RediSep C18, 360 g) using a water ethanol gradient (100 mL/min) as below:

TABLE 5

| Time | % ethanol |
|---|---|
| 0 | 0 |
| 10 | 0 |
| 27.1 | 70.2 |
| 27.5 | 76.6 |
| 28 | 100 |
| 35.6 | 100 |
| 35.6 | 100 |
| 35.6 | 50 |
| 40.3 | 50 |
| 40.7 | 50 |

A total of 628 mg of steviol glycosides were recovered. Of that sample 18 mg were recovered comprising about 23% Rebaudioside D, 21% Rebaudiosides N and M, 1.4% uncharacterized steviol glycosides, 2% Rebaudioside A and about 16% other known steviol glycosides. The solid had an off-white to beige appearance and had a clean sweet taste. The product is suitable for use as a sweetening agent without further processing or purification.

TABLE 6

| Time (minutes) | Mass (mg) | Composition (by HPLC/CAD) | Sample Appearance | Taste (by 2 indep. assessments) |
|---|---|---|---|---|
| 22.8-23.6 | 78 | Non-steviol glycoside components | Light beige solid | Bitter (not sweet) |
| 23.6-25 | 18 | Predominantly Reb. D, N, M | Med. Brown solid | Clean sweet taste |
| 26-31.5 | 610 | Reb. A and smaller steviol glycosides | Light yellow solid | "classic" Reb. A taste, i.e., sweet with bitter notes |

Example

The remaining extract was concentrated under vacuum at less than 40° C. clarified by centrifugation, decanted, cooled. An aliquote (53 mL, 9.5 g solids) of the concentrate was withdrawn for fractionation. The major portion was dried by lyophilization to yield 65.3 g of solids. The concentrate was directly fractionated on a preparative scale reverse-phase column (RediSep C18, 360 g) using a water-ethanol gradient. (100 mL/min) as below:

TABLE 7

| Time | % Ethanol |
|---|---|
| 0 | 0 |
| 10 | 0 |

TABLE 7-continued

| Time | % Ethanol |
|---|---|
| 19.8 | 39.9 |
| 32 | 100 |
| 37.5 | 100 |
| 41 | 100 |
| 41 | 45.2 |
| 44.7 | 45.2 |
| 50 | 45.2 |

Approximately 4.3 g of steviol glycosides were recovered. The majority of the rebaudioside D eluting at about 25 minutes (1.6 g; 18% rebaudioside D and 5% rebaudioside A) with some non-steviol glycoside components. The majority of the rebaudioside A eluting at 27 minutes (2.2 g; 78% rebaudioside A and 1% rebaudioside D).

Example

Authentic samples of Rebaudiosides A (0.5 g) and D (0.5 g) were separated on the same system using a more gradual gradient as indicated below:

TABLE 8

| Time (minutes) | % Ethanol |
|---|---|
| 0 | 0 |
| 10 | 0 |
| 38.2 | 100 |
| 44.1 | 100 |
| 44.1 | 50 |
| 50 | 50 |

An improved separation was obtained with the major portion of rebaudioside D eluting at 28 minutes (2.40 mg; 86% reb. D, 9.3% reb. A), and the major portion of rebaudioside A eluding at 31 minutes (372 mg; 89% reb. A. 3% reb. D).

The steviol glycosides obtained according to this invention may be incorporated as a high intensity natural sweetener in foodstuffs, beverages, pharmaceutical compositions, cosmetics, chewing gums, table top products, cereals, dairy products, toothpastes and other oral cavity compositions, etc. The examples above show representative proportions which may be employed.

In addition, the steviol glycosides can be used as a sweetener not only for drinks, foodstuffs, and other products dedicated for human consumption, but also in animal feed with improved characteristics.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

The sweetener obtained in this invention can be used in dry or liquid forms. It can be added before or after heat treatment of food products. The amount of the sweetener depends on the purpose of usage. It can be added alone or in the combination with other compounds.

TABLE 9 shows the chemical structure of steviol and the steviol glycosides present in the Stevia rebaudiana Bertoni leaves.

U.S. Patent Oct. 30, 2012 Sheet 1 of 11 U.S. Pat. No. 8,299,224 B2

FIG. 1

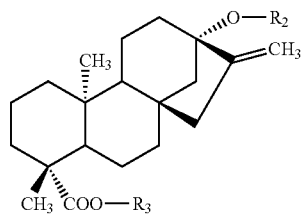

| Compound name | $R_1$(C-19) | $R_2$(C-13) |
|---|---|---|
| 1. Steviol | H | H |
| 2. Steviolmonoside | H | β-Glc |
| 3. Ruboside | β-Glc | β-Glc |
| 4. Steviolbioside | H | β-Glc-β-Glc(2→1) |
| 5. Stevioside | β-Glc | β-Glc-β-Glc(2→1) |
| 6. Rebaudioside B | β-Glc | β-Glc-β-Glc(2→1)<br>\|<br>β-Glc(3→1) |
| 7. Rebaudioside B | H | β-Glc-β-Glc(2→1)<br>\|<br>β-Glc(3→1) |
| 8. Rebaudioside C (Dulcoside B) | β-Glc | β-Glc-α-Rha(2→1)<br>\|<br>β-Glc(3→1) |
| 9. Rebaudioside D | β-Glc-β-Glc(2→1) | β-Glc-β-Glc(2→1)<br>\|<br>β-Glc(3→1) |
| 10. Rebaudioside E | β-Glc-β-Glc(2→1) | β-Glc-β-Glc(2→1) |
| 11. Rebaudioside F | β-Glc | β-Glc-β-Xyl(2→1)<br>\|<br>β-Glc(3→1) |
| 12. Dulcoside A | β-Glc | β-Glc-α-Rha(2→1) |

TABLE 10

Proposed structures and their relative percentage of the steviol glycosides from the leaves of *S. rebaudiana* Morita and *S. rebaudiana* Bertoni.

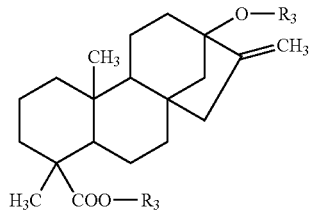

| Steviol Glycoside | $R_1$ | $R_2$ | Morita (%)[1] | Bertoni (%)[1,2] |
|---|---|---|---|---|
| SG1 (steviolmonoside) | H— | Glcβ1- | 1.7 | 1.7 |
| SG2 (steviolbioside) | H— | Glcβ1-2Glcβ1- | 1.0 | 5.0 |
| SG3 (rubusoside) | Glcβ1- | Glcβ1- | 0.8 | ND[3] |
| SG4 (dulcoside B)[4] | H— | Rhaα1-2(GlcB1-3)Glcβ1- | 0.6 | 0.8 |
| SG5 (dulcoside A) | Glcβ1- | Rhaα1-2Glcβ1- | 0.3 | 2.6 |
| SG6 (rebaudioside B) | H— | Glcβ1-2(Glcβ1-3)Glcβ1- | 2.5 | 2.0 |
| SG7 (rebaudioside G)[4] | Glcβ1- | Glcβ1-3Glcβ1- | 1.1 | 0.8 |
| SG8 (stevioside) | Glcβ1- | Glcβ1-2Glcβ1- | 9.2 | 49.8 |
| SG9 (rebaudioside C) | Glcβ1- | Rhaα1-2(Glcβ1-3)Glcβ1- | 7.5 | 6.8 |
| SG10 (rebaudioside F) | Glcβ1- | Xylβ1-2(Glcβ1-3)Glcβ1- | 1.9 | 1.4 |
| SG11 (rebaudioside A) | Glcβ1- | Glcβ1-2(Glcβ1-3)Glcβ1- | 61.6 | 21.5 |
| SG12 (rebaudioside I)[4] | Glcβ1-3Glcβ1- | Glcβ1-2(Glcβ1-3)Glcβ1- | 0.1 | ND[3] |
| SG13 (rebaudioside E) | Glcβ1-2Glcβ1- | Glcβ1-2Glcβ1- | 0.3 | 0.9 |
| SG14 (rebaudiodide H)[4] | Glcβ1- | Glcβ1-3Rhaα1-2(Glcβ1-3)Glcβ1- | 0.5 | ND[3] |
| SG15 (rebaudioside L)[4] | Glcβ1- | Glcβ1-6G1cβ1-2(Glcβ1-3)Glcβ1- | 0.3 | ND[2] |
| SG16-I (rebaudioside K)[4] | Glcβ1-2Glcβ1- | Rhaα1-2(Glcβ1-3)Glcβ1- | 0.3 | ND[3] |
| SG16-II (rebaudioside J)[4] | Rhaα1-2Glcβ1- | Glcβ1-2(Glcβ1-3)Glcβ1- | 0.5 | 0.1 |
| SG17 (rebaudioside M)[4] | Glcβ1-2(Glcβ1-3)Glcβ1 | Glcβ1-2(Glcβ1-3)Glcβ1- | 1.0 | ND[3] |
| SG18 (rebaudioside D) | Glcβ1-2Glcβ1- | Glcβ1-2(Glcβ1-3)Glcβ1- | 2.1 | 0.4 |
| SG19 (rebaudioside N)[4] | Rhaα1-2(Glcβ1-3)Glcβ | Glcβ1-2(Glcβ1-3)Glcβ1- | 1.4 | <0.1 |
| SG20 (rebaudioside O)[4] | Glcβ1-3Rhaα1-2(Glcβ1-3)Glcβ1- | Glcβ1-2(Glcβ1-3)Glcβ1- | 0.6 | ND[3] |

*From Ohta et al. (2010).
[1]Relative amounts are expressed as percentage of total peak areas detected on the basis of their UV absorbance at 210 nm by Amide-SO/HPLC. The ratio of SG16-I and SG16-II was obtained by the relative intensities of the product ions at m/z 787 and 803, respectively, by the CID voltage of 60 V in ESI-MS/MS analysis as precursor ion [M − H]⁻ at m/z 1111.
[2]The structures were proposed on the basis of the results on HPLC mobility and ESI-MS and MS/MS analyses.
[3]Not detected.
[4]Names were proposed in this study.

The invention claimed is:

1. A process for production a steviol glycoside composition comprising:
   a) extracting dried *Stevia* leaves for 2 h at 95° C. to form a crude extract;
   b) fractionating the crude extract on a reverse-phase column, wherein fractionation is conducted using a gradient of water and ethanol, wherein said gradient is used starting from 1:0, moving to 29.8:70.2, moving to 23.4:76.6, moving to 0:1, and moving to 1:1 water to ethanol, where the ethanol is food grade ethanol; wherein, fractions containing rebaudioside D, N, M, and A are collected and the water and ethanol removed, to provide a steviol glycoside composition comprising 23% rebaudioside D, 21% rebaudiosides N and M, and 2% rebaudioside A; and wherein, rebaudiosides D, N, M, and A are obtained in the claimed percentages without the need for crystallization.

2. The process of claim 1, wherein the *Stevia* leaves have not been desiccated.

3. The process of claim 1, wherein the *Stevia* leaves have been desiccated.

4. The process of claim 1, wherein the resulting composition further comprises one or more of rebaudiosides I and O.

5. The process of claim 1, wherein the crude extract is clarified by centrifugation or filtration before fractionation.

* * * * *